United States Patent
Lu et al.

(10) Patent No.: US 10,131,794 B2
(45) Date of Patent: *Nov. 20, 2018

(54) NETWORK COPOLYMER CROSSLINKED COMPOSITIONS AND PRODUCTS COMPRISING THE SAME

(75) Inventors: Ning Lu, Chappaqua, NY (US);
Sigfredo Gonzalez, Danbury, NY (US);
Ernie Silvestre, Yonkers, NY (US);
Geng Wang, Vienna, WV (US)

(73) Assignee: Momentive Performance Materials Inc., Waterford, NY (US)

( * ) Notice: Subject to any disclaimer, the term of this patent is extended or adjusted under 35 U.S.C. 154(b) by 557 days.

This patent is subject to a terminal disclaimer.

(21) Appl. No.: 12/975,885

(22) Filed: Dec. 22, 2010

(65) Prior Publication Data

US 2011/0152083 A1   Jun. 23, 2011

Related U.S. Application Data

(60) Provisional application No. 61/289,782, filed on Dec. 23, 2009.

(51) Int. Cl.
| | | |
|---|---|---|
| *A61K 8/81* | (2006.01) | |
| *A61Q 19/00* | (2006.01) | |
| *C09D 4/00* | (2006.01) | |

(52) U.S. Cl.
CPC ..................................... *C09D 4/00* (2013.01)

(58) Field of Classification Search
None
See application file for complete search history.

(56) References Cited

U.S. PATENT DOCUMENTS

| | | | |
|---|---|---|---|
| 2002/0052459 A1 | 5/2002 | Kohlhammer et al. | |
| 2003/0144399 A1 | 7/2003 | Matta et al. | |
| 2005/0196432 A1* | 9/2005 | Munro et al. | 424/445 |
| 2006/0141392 A1* | 6/2006 | Yoon et al. | 430/270.1 |
| 2007/0060729 A1* | 3/2007 | Kim et al. | 526/274 |
| 2008/0281038 A1 | 11/2008 | Takahashi et al. | |
| 2009/0136872 A1 | 5/2009 | Yoon et al. | |

FOREIGN PATENT DOCUMENTS

WO   2008013417 A1   1/2008

OTHER PUBLICATIONS

Wu, Shobing et al., "Effects of sulphonic and phosphonic acrylic monomers on the crosslinking of acrylic latexes with cycloaliphatic epoxide", Progress in Organic Coatings 36 (1999), pp. 21-33 (XP-002649727).

* cited by examiner

*Primary Examiner* — Thor B Nielsen
(74) *Attorney, Agent, or Firm* — Joseph S. Ostroff

(57) ABSTRACT

The present invention provides for a household, agricultural, coating or personal care product composition containing the crosslinked reaction product of a network composition the reaction product of: (i) at least one anionic polymerizable ethylenically unsaturated monomer (I) selected from the group consisting of

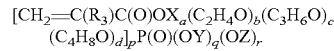

and

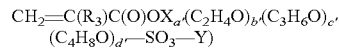

where $R_3$=H or alkyl of 1 to about 6 carbon atoms; X=alkyl, aryl, or alkaryl diradical connecting group of 0 to about 9 carbon atoms; a, a', b, b', c, c', d and d' are 0 to about 100; q is 0 to about 2; r is 0 to about 2; p is 1 to about 3 subject to the limitation that p+q+r=3; and Y and Z is H, or metal ion; and (ii) one or more additional monomers (II) selected from the group consisting of acrylic acid/acrylate, methacrylic acid/methacrylate, acrylamides, vinyl acetate and styrene, which are copolymerizable with (I); and (iii) a cross-linking agent (III), capable of copolymerizing with (I) and (II).

16 Claims, No Drawings

NETWORK COPOLYMER CROSSLINKED COMPOSITIONS AND PRODUCTS COMPRISING THE SAME

CROSS REFERENCE TO RELATED APPLICATIONS

This application claims priority to U.S. provisional application No. 61/289,782 filed Dec. 23, 2009, which is herein incorporated by reference.

FIELD OF THE INVENTION

The present invention relates to network copolymer compositions, processes for their preparation, and products comprising the same.

BACKGROUND OF THE INVENTION

Network copolymer compositions can exhibit a variety of physical properties. The polymers can be modified to be hydrophilic, lipophilic and hydrophobic depending on the nature of the organic substituents. Recently, network compositions have been made by simultaneously polymerizing and cross-linking, in the presence of a free radical polymerization catalyst of a mixture of polymeizable ethylenically unsaturated monomers having particular structures that have shown utility in a variety of applications including personal care (hair conditioners, skin care and color cosmetics), textile treatments, hard surface modifiers, agricultural adjuncts, and the like. These compositions are further described and claimed below. In addition, particular methods of making these products are also shown and claimed below.

SUMMARY OF THE INVENTION

According to the invention, there is provided an agricultural, personal care or household product comprising a network copolymer composition comprising the reaction product of:

i) at least one anionic polymerizable ethylenically unsaturated monomer (I) selected from the group consisting of

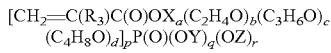

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 to about 2;
r is 0 to about 2;
p is 1 to about 3 subject to the limitation that p+q+r=3; and Y and Z is H, or metal ion;
and

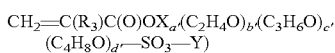

where
$R_3$=H or alkyl of from 1 to about 6 carbon atoms;
X=alkyl, aryl, or alkaryl diradical connecting group of 0 to about 9 carbon atoms;
a' is 0 to about 100;
b' is 0 to about 100;
c' is 0 to about 100;
d' is 0 to about 100;
Y is H, or metal ion; and (ii) one or more additional monomers (II) selected from the group consisting of acrylic acid/acrylate, methacrylic acid/methacrylate, acrylamides, vinyl acetate and styrene, which are copolymerizable with (I); and (iii) a cross-linking agent (III), capable of copolymerizing with (I) and (II).

Another aspect of the present invention is directed to an agricultural, personal care or household product comprising the reaction product described above wherein the cross-linking agent (III) is at least one anionic polymerizable ethylenically unsaturated monomer (I) selected from the group consisting of

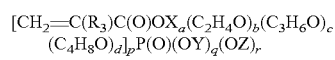

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 to about 2;
r is 2 or 3; and
p is 1 to about 3 subject to the limitation that p+q+r=3; Y and Z is H, or metal ion.

Still yet another aspect of the present invention is directed to an agricultural, personal care or household product comprising the reaction product described above wherein monomer (I) is selected from the group consisting of $CH_2$=C$(CH_3)$C(O)O$(C_3H_6O)_6$P(O)(OH)(ONa), $CH_2$=C$(CH_3)$C(O)O$(C_3H_6O)_6$P(O)(OH)$_2$, $CH_2$=CHC(O)O$(C_3H_6O)_6$P(O)(OH)(OH)$_2$, $CH_2$=C$(CH_3)$C(O)O$(C_2H_4O)_n$P(O)(OH)$_2$ and combinations thereof;
said additional monomers (II) are selected from the group consisting of: $CH_2$=CHC(O)OH, $CH_2$=C$(CH_3)$C(O)O$(C_3H_6O)_6$H and combinations thereof; and said cross-linking agent (III) is selected from the group consisting of $CH_2$=CHC(O)O$(C_2H_4O)_n$C(O)OCH=$CH_2$), $CH_2$=C$(CH_3)$CO$_2$CH$_2$]$_3$CC$_2$H$_5$, [$CH_2$=C$(CH_3)$C(O)O$(C_3H_6O)_6$]$_2$P(O)(OH) and combinations thereof.

Additional embodiments are also part of the present invention, which are further described in the Detailed Description of the Invention below.

DETAILED DESCRIPTION OF THE INVENTION

The present invention provides an agricultural, personal care or household product containing a network composition comprising the reaction product of:

i) at least one anionic polymerizable ethylenically unsaturated monomer (I) selected from the group consisting of

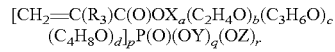

where
$R_3$=H or alkyl of 1 to about 6 carbon atoms;
X=alkyl, aryl, or alkaryl diradical connecting group of 0 to about 9 carbon atoms; a is 0 to about 100, 1 to about 100, preferably 0 to about 40 and more preferably about 0 to about 15;
b is 0 to about 100, 1 to about 100, preferably 0 to about 40 and more preferably about 0 to about 15;
c is 0 to about 100, 1 to about 100, preferably 0 to about 40 and more preferably about 0 to about 15;

d is 0 to about 100, 1 to about 100, preferably 0 to about 40 and more preferably about 0 to about 15;
q is 0 to about 2;
r is 0 to about 2;
p is 1 to about 3 subject to the limitation that p+q+r=3; and
Y is H, or metal ion;
and

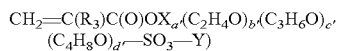

where
$R_3$=H or alkyl of from 1 to about 6 carbon atoms;
X=alkyl, aryl, or alkaryl diradical connecting group of 0 to about 9 carbon atoms;
   a' is 0 to about 100, 1 to about 100, preferably 0 to about 40 and more preferably about 0 to about 15;
   b' is 0 to about 100, 1 to about 100, preferably 0 to about 40 and more preferably about 0 to about 15;
   c' is 0 to about 100, 1 to about 100, preferably 0 to about 40 and more preferably about 0 to about 15;
   d' is 0 to about 100, 1 to about 100, preferably 0 to about 40 and more preferably about 0 to about 15;
   Y and Z is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I); and
(iii) a cross-linking agent (III), capable of copolymerizing with (I) and (II).

In one embodiment of the present invention the agricultural, personal care or household product comprising a network composition described above includes up to about 0.5 to about 50 percent by weight of the total weight of monomers, of one or more additional monomer, preferable any acrylic acid/acrylate, methacrylic acid/methacrylate, or monomers such as acrylamides, vinyl acetate and styrene, which are copolymerizable with (i). Any organic acrylate or methacrylate can be employed as the comonomers in the composition. Examples of such monomers include, but are not limited to, acrylic acid and methacrylic acid or the derivatives such as methyl, ethyl, butyl, amyl, 2-ethylhexyl, cyclohexyl, vinyl, ally, hydroxyethyl, perfluoroethyl, isobornyl, phenoxyethyl, tetraethylene glycol, tripropylene glycol, trimethylolpropane, polyoxyalkylene.

According to still another aspect of the present invention further provides an agricultural, personal care or household product comprising a network composition as described above wherein the cross-linking agent is polyfunctional vinlyidene monomer containing at least two unsaturated groups. Examples of polyfunctional vinylidene monomers of the network composition is selected from group consisting of butadiene, isoprene, divinyl benzene, allyl acrylates, polyalkylene glycol diacrylates and dimethacrylates. Other crosslinking agents include diallyl esters and dimethallyl esters and other crosslinking agents listed and described in U.S. Pat. No. 4,509,949 herein incorporated in its entirety by reference.

In still yet another aspect of the present invention, an agricultural, personal care or household product comprising a network composition as described above wherein the composition comprises about 40 to about 99, preferably 50 to about 85, more preferably about 60 to about 75 weight percent based on the total weight of the monomers of at least one anionic polymeriazable ethylenically unsaturated monomer (I), about 0.5 to about 50, preferably about 5 to about 40, more preferably about 10 to about 30 percent based on the total weight of the monomers of the additional monomers and about 0.1 to about 10, preferably about 2 to about 8, more preferably about 3 to about 6 weight percent based on the total weight of the monomers of said cross-linking agent.

Both the acrylate cross-links and the polyether substituents are capable of hydrogen bonding with water and other hydroxylic solvents, increasing content of either, all other composition variables remaining constant, will tend to increase the water swellability of the resulting cross-linked network polymer. Because it is possible to vary the compositional parameters of the cross-linked network copolymers of the invention in an almost limitless fashion, some compositions are both water swellable and oil swellable while others are only water swellable or oil swellable, and some compositions will not be swellable with any of the solvents discussed herein. The amount of crosslinking present in the crosslinked network may be characterized with respect to the degree of swelling exhibited by the network in the fluid.

The cross-linked structure of the agricultural, personal care or household product comprising network of the present invention is effective to allow the network to be swollen from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the composition of the present invention to leave the original volume, that is, the volume of the copolymer network in the absence of the fluid.

According to yet another aspect of the present invention, the network composition of the agricultural, personal care or household product of the present invention comprising comprises a reaction product of monomer (I) provided below and has a subscript p equal to 2 or 3, no additional cross linking agent is necessary. That is, an agricultural, personal care or household product is provided comprising a network composition comprising at least one anionic polymerizable ethylenically unsaturated monomer (I)

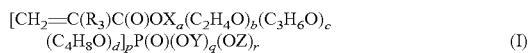

where
$R_3$=H or alkyl of 1 to about 6 carbon atoms;
X=alkyl, aryl, or alkaryl diradical connecting group of 0 to about 9 carbon atoms; a is 0 to about 100;
b is 0 to about 100;
c is 0 to about 100;
d is 0 to about 100;
q is 0 to about 2;
r is 2 or 3;
p is 1 to about 3 subject to the limitation that p+q+r=3; and
Y and Z is H, or metal ion; and
(ii) one or more additional monomers (II) selected from the group consisting of acrylic acid/acrylate, methacrylic acid/methacrylate, acrylamides, vinyl acetate and styrene, which are copolymerizable with (I). No additional cross-linking agent is necessary for the reaction of monomer (I) and monomer (II) in this embodiment of the present invention since monomer (I) having a p value of 2 or 3 is essentially a polyunsaturated molecule having 2 or 3 double bonds and therefore acts as a cross-linking agent.

In one embodiment of the present invention, the network composition of the agricultural, personal care or household product of the present invention comprises is a solid, typically having a creamy consistency, wherein the copolymer network acts as a means for gelling the fluid to reversibly impart characteristics of a solid to the fluid. At rest, the composition exhibits the properties of a solid gel material.

The composition of the present invention exhibits high stability and resistance to syneresis, that is, the composition exhibits little or no tendency for fluid to flow from the composition and imparts high stability and syneresis resistance to personal care compositions, which include the composition as a component. The high stability and syneresis resistance persists with prolonged aging of such compositions and personal care compositions. However, fluid may be released from the network by subjecting the composition to a shearing force, such as, for example, by rubbing the composition between one's fingers, to provide improved sensory feel characteristic of the fluid component of the material.

Water (or a water equivalent such as a non-aqueous hydroxylic solvent), siloxane, linear or cyclic, or lipophillic fluid (oil swelling agent, oil swellable) may be used as the swelling agent. Lipophilic fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In another embodiment of the invention, the copolymer network is a crosslinked network that is insoluble in various fluid components, but that is capable of being swollen by the fluid. The amount of crosslinking present in the crosslinked network may be characterized with respect to the degree of swelling exhibited by the network in the fluid. In another preferred embodiment, the crosslinked structure of the network is effective to allow the network to be swollen by water, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the composition of the present invention to leave the original volume, that is, the volume of the copolymer network in the absence of the fluid. In another preferred embodiment, the crosslinked structure of the network is effective to allow the network to be swollen by a lipophilic fluid, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the composition of the present invention to leave the original volume, that is, the volume of the copolymer network in the absence of the fluid.

In another preferred embodiment, the crosslinked structure of the network in the agricultural, personal care or household product comprising is effective to allow the network to be swollen by a low molecular weight silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the composition of the present invention to leave the original volume, that is, the volume of the copolymer network in the absence of the fluid.

In yet another embodiment of the present invention, the fluid component of the agricultural, personal care or household product of the present invention comprises an emollient compound. Suitable emollient compounds include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as, for example, oleyl alcohol and isomyristyl alcohol.

According to yet another aspect an agricultural, personal care or household product is provided that comprises a network composition comprising the reaction product of at least one anionic polymerizable ethylenically unsaturated monomer (I) selected from the group consisting of $CH_2\!=\!C(CH_3)C(O)O(C_3H_6O)_6P(O)(OH)(ONa)$, $CH_2\!=\!C(CH_3)C(O)O(C_3H_6O)_6P(O)(OH)_2$, $CH_2\!=\!CHC(O)O(C_3H_6O)_6P(O)(OH)(OH)_2$, and $CH_2\!=\!C(CH_3)C(O)O(C_2H_4O)_nP(O)(OH)_2$ and combinations thereof; additional monomers (II) selected from the group consisting of: $CH_2\!=\!CHC(O)OH$ and $CH_2\!=\!C(CH_3)C(O)O(C_3H_6O)_6H$ and combinations thereof; and cross-linking agent (III) selected from the group consisting of $CH_2\!=\!CHC(O)O(C_2H_4O)_nC(O)OCH\!=\!CH_2)$, $CH_2\!=\!C(CH_3)CO_2CH_2]_3CC_2H_5$, $[CH_2\!=\!C(CH_3)C(O)O(C_3H_6O)_6]_2P(O)(OH)$ and combinations thereof.

Examples of solvents that can be used in the agricultural, personal care or household product of the present invention include but are not limited to silicone fluid, water, alcohol, ester, hydrocarbon fluid or organic oil. Examples of catalyst that can be used in making the network composition used in the agricultural, personal care or household product of the present invention include but are not limited to free radical catalysts such as peroxides such as hydrogen peroxide, ammonium persulfate, potassium persulfate and the like. Organic peroxy catalysts, such as dialkyl peroxides, e.g., diisopropyl peroxide, dilauryl peroxide, di-t-butyl peroxide, dicumyl peroxide, alkyl hydrogen peroxides such as t-butyl hydrogen peroxide, t-amyl hydrogen peroxide, cumyl hydrogen peroxide, diacyl peroxide, for instance acetyl peroxide, lauroyl peroxide, benzoyl peroxide, peroxy ester such as ethyl peroxybenzoate, pavalate peroxide, the azo compounds such as 2-azobis(isobutyronitrile), 1-azobis(1-cyclohexanecarbonitrile) and the like and other free radical generating catalysts.

The network polymer composition used in the agricultural, personal care or household product of the present invention may be further processed under low or high shear to adjust the viscosity and sensory feel of the composition. This may be achieved, for example, by subjecting the composition to a moderate to high shearing force. Optionally, one or more fluids may be added to the silicone composition prior to the shearing. The network polymer composition of the present invention may be in a gel form, which contains the polymer itself and the solvents. It can also be processed (i.e. evaporated) to remove part or all of the solvents.

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges. As used herein, integer values of stoichiometric subscripts refer to molecular species and non-integer values of stoichiometric subscripts refer to a mixture of molecular species on a molecular weight average basis, a number average basis or a mole fraction basis. In the case of mixtures of the compounds of the present invention, it should be readily apparent that the stoichiometric subscripts of mixtures would have average values for the subscripts that may be either integral or non-integral in contrast to those of pure compounds.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "cross-linked polymers" means polymer molecules which are built from monomers which are linked together at many points other than their ends and as a result molecules with large size form and the material is non-pourable solid or gel-like which cannot be dissolved in any solvent. Cross-links are bonds that link one polymer chain to another. They can be covalent bonds or ionic bonds. "Polymer chains" can refer to synthetic polymers or natural polymers. In synthetic polymers, crosslinking refers to the use of cross-links to promote a difference in the polymers' physical properties.

The copolymers in our invention are "non-crosslinked", which means that their monomers are either not linked together at points other than their ends or the linkages between the polymers are so few that the copolymer is either liquid or can be dissolved in at least one solvent.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the present invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Other optional ingredients may be added in the compositions of the present invention including coupling agents, e.g., silane coupling agents, curing aids, e.g., including activators, retarders and accelerators, processing additives such as oils, plasticizers, tackifying resins, silicas, other fillers, pigments, fatty acids, zinc oxide, waxes, antioxidants and anti-ozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

The compositions of the present invention can be used commercially as a demulsifying agents, in agricultural compositions including fertilizers, in cosmetics and personal care products, in household cleaners, in coating compositions such as waxes and the like, in water processing apparatuses as well as other products.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Other optional ingredients may be added in the compositions of the present invention including coupling agents, e.g., silane coupling agents, curing aids, e.g., including activators, retarders and accelerators, processing additives such as oils, plasticizers, tackifying resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

Applications for Embodiments of the Invention

A. Agricultural Uses

Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces; enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticide compositions of the present invention also include at least one pesticide, where the network copolymers of the present invention is present at an amount sufficient to deliver between 0.005% and 2% to the final use concentration, either as a concentrate or diluted in a tank mix. Optionally the pesticide composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and Micronutrients:

Fertilizers and micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, and calcium chloride.

The pesticide or fertilizer may be a liquid or a solid. If a solid, it is preferable that it is soluble in a solvent, or the organomodified disiloxanes of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4 trimethyl, 1 3 pentane diol and alkoxylated (especially ethoxylated) versions thereof as illustrated in U.S. Pat. No. 5,674,832 herein incorporated by reference, or n-methyl-pyrrolidone.

Cosurfactants:

Cosurfactants useful herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful. Additionally, the compositions described above are also useful as the alkyl chloride, alkyl iodide and alkyl bromide analogues, as well as the acid pairs with HCl, acetic acid, propionic acid, glycolic acid, gibberellic acid and the like. One skilled in the art understands the benefits of quaternization, which increases solubility and as well as makes possible potential interactions with nonionic and anionic cosurfactants.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—Air Products), pyrrilodone based surfactants (e.g., SURFADONE—LP 100—ISP), 2-ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as ChoiceÒ (Loveland Industries, Greeley, Colo.) and Quest (Helena Chemical, Collierville, Tenn.), modified clays such as SurroundÒ (Englehard Corp.,), foam control agents, surfactants, wetting agents, dispersants, emulsifiers, deposition aids, antidrift components, and water.

Suitable agrochemical compositions are made by combining, in a manner known in the art, such as, by mixing one or more of the above components with the organomodified disiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

B. Coatings

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as, solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, Alkyds, Acrylics, Epoxies

C. Personal Care

The non-crosslinked copolymer compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the copolymers of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the compositions of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the copolymers of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex glycine.

In another useful embodiment, a skin care composition comprises the compositions of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butyl methoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the compositions of the present invention, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions; other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

E. Water Processing

Compositions comprising the non-crosslinked copolymers of the present invention are useful for applications involving commercial and industrial open recirculating cooling water towers, closed cooling water systems, cooling water conduits, heat exchangers, condensers, once-through cooling systems, Pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

F. Pulp and Paper

Compositions of the present invention are useful in pulp and paper applications, such as paperboard defoamers, ink removal agents, and wetting agents for the pulping process.

SYNTHETIC EXAMPLES

Example 1

Preparation Network Polymer Composition 1

Mixture through 1 through 4 in Table I were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5-minute time period. The mixture was cooled to 25 C after two hours. Mixture 4 was then added and the mixture was mixed for 30 minutes to give an off-white soft solid.

TABLE I

| INGREDIENTS | WEIGHT (grams) |
| --- | --- |
| Mixture 1 | |
| Trimethylolpropane trimethacrylate | 0.2 |
| Acrylic acid | 3.9 |
| Phosphate mono-ester of polypropylene glycol mono-methacrylate (MW = 500) | 151.2 |
| Phosphate di-ester of polypropylene glycol mono-methacrylate (MW = 900) | 15.4 |
| Polyproplyeneglycol mono-methacrylate (MW = 400) | 8.4 |
| Tergital TMN-6 | 7.0 |
| Water | 443.8 |
| Sodium hydroxide solution (40 wt % in water) | 39.7 |
| Mixture 2 | |
| Sodium bisulfite solution (10% in water) | 1.8 |
| Ferrous ammonium sulfate solution (0.2% in water) | 3.5 |
| Mixture 3 | |
| Potassium persulfate solution (4.5 wt % in water) | 21.0 |
| Mixture 4 | |
| Sodium metabisulfite solution (10 wt % in water) | 35.0 |

*Tergital TMN-6 is a Branched Secondary Alcohol Ethoxylates, available at Dow Chemicals.

Example 2

Preparation of Network Polymer Composition II

Mixture 1 through 4 in Table II were used to prepare Network Polymer Composition I. Mixer 1 was placed in a 2 L IRA mixer. Nitrogen was bubbled through for 30 minutes to remove oxygen from the system. The mixture was heated to 55° C. under nitrogen and held at the temperature. Mixture 2 and mixture 3 were added over a 5- minute time period. The mixture was cooled to 25° C. after two hours. Mixture 4 was then added and the mixture was mixed for 30 minutes to give an off-white soft solid.

TABLE II

| INGREDIENTS | WEIGHT (grams) |
|---|---|
| Mixture 1 | |
| Phosphate mono-ester of polypropylene glycol mono-methacrylate (MW = 500) | 108.0 |
| Phosphate di-ester of polypropylene glycol mono-methacrylate (MW = 900) | 11.0 |
| Polyproplyeneglycol mono-methacrylate (MW = 400) | 6.0 |
| *Tergital TMN-6 | 5.0 |
| **Sag 330 | 0.3 |
| Water | 314.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals.
**Sag 330 is a silicone-based antifoam emulsion, available at Momentive Performance Materials.

Example 3

Preparation of Network Polymer Composition III

Part 1 through 3 in Table III were used to prepare Network Polymer Composition III. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE III

| INGREDIENTS | WEIGHT (grams) |
|---|---|
| Part 1 | |
| Phosphate mono-ester of polypropylene glycol mono-methacrylate (MW = 500) | 25.9 |
| Phosphate di-ester of polypropylene glycol mono-methacrylate (MW = 900) | 2.6 |
| Polyproplyeneglycol mono-methacrylate (MW = 400) | 1.4 |
| Water | 70.0 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 4

Preparation of Network Polymer Composition IV

Part 1 through 3 in Table IV were used to prepare Network Polymer Composition IV. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE IV

| INGREDIENTS | WEIGHT (grams) |
|---|---|
| Part 1 | |
| Polyethyleneglycol diacrylate | 0.08 |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |
| Part 2 | |
| Sodium bisulfite | 0.15 |
| Part 3 | |
| Potassium persulfate | 0.3 |

Example 5

Preparation of Network Polymer Composition V

Part 1 through 3 in Table V were used to prepare Network Polymer Composition V. The ingredients in Part 1 were placed mixed under nitrogen. Nitrogen was bubbled for 30 minutes to remove oxygen from the system. The mixture was heated to 50° C. and held at that temperature. Part 2 and Part 3 were added into Part 1 at 50° C. The mixture was heated at 55° C. for approximated three hours to give an off-white soft solid.

TABLE V

| INGREDIENTS | WEIGHT (grams) |
|---|---|
| Part 1 | |
| Acrylic acid | 0.55 |
| Phosphate mono-ester of polypropylene glycol mono-methacrylate (MW = 500) | 21.6 |
| Phosphate di-ester of polypropylene glycol mono-methacrylate (MW = 900) | 2.2 |
| Polyproplyeneglycol mono-methacrylate (MW = 400) | 1.2 |
| Water | 74.4 |
| Sodium hydroxide solution (40 wt % in water) | q.s. to pH 5 |

TABLE V-continued

| INGREDIENTS | WEIGHT (grams) |
|---|---|
| Part 2 | |
| Sodium bisulfite solution | 0.15 |
| Part 3 | |
| Potassium persulfate | 0.3 |

Example 6

Use of Network Polymer Composition I as an Aqueous Phase Thickener

The thickened aqueous compositions of Example 6 were made by combining the listed ingredients in the relative amounts set forth in Table VI, according to the following procedures. Network Polymer Composition I prepared according to Example 1 was missed with D.I. water using an overhead mixer at 700 RPM for 10 minutes. The viscosities of the resulting materials (measured after 24 hours) are listed in Table VI.

TABLE VI

| | Sample 6-1 | Sample 6-2 | Sample 6-3 | Sample 6-4 |
|---|---|---|---|---|
| Ingredients | | | | |
| Network polymer composition I (grams) | 8.3 | 10 | 11.7 | 13.3 |
| Water (grams) | 41.7 | 40 | 38.3 | 36.7 |
| Property | | | | |
| Viscosity (cPs) | 4000 | 15000 | 128000 | 216500 |

Example 7

Use of Network Polymer Composition II as an Aqueous Phase Thickener

The thickened aqueous compositions of Example 7 were made by combining the listed ingredients in the relative amounts set forth in Table VII, according to the following procedures. Network Polymer Composition II prepared according to Example 2 was missed with D.I. water using an overhead mixer at 700 RPM for 10 minutes. The viscosities of the resulting materials (measured after 24 hours) are listed in Table VII.

| | Sample 7-1 | Sample 7-2 | Sample 7-3 | Sample 7-4 |
|---|---|---|---|---|
| Ingredients | | | | |
| Network polymer composition II (grams) | 7.1 | 8.3 | 10 | 12.5 |
| Water (grams) | 42.9 | 41.7 | 40 | 37.5 |
| Property | | | | |
| Viscosity (cPs) | 22000 | 40500 | 71000 | 105500 |

Example 8

Use of Network Polymer Composition III, IV and V as Aqueous Phase Thickeners

The thickened aqueous compositions of Example 8 were made by combining the listed ingredients in the relative amounts set forth in Table VIII, according to the following procedures. Network Polymer Composition III, IV and V were prepared according to Example 3, 4 and 5 respectively. The ingredients were mixed using an overhead mixer at 700 RPM for 10 minutes. The viscosities of the resulting materials (measured after 24 hours) are listed in Table VIII.

TABLE VIII

| | Sample 8-1 | Sample 8-2 | Sample 8-3 |
|---|---|---|---|
| Ingredients | | | |
| Network polymer composition III (grams) | 16.7 | | |
| Network polymer composition IV (grams) | | 16.7 | |
| Network polymer composition V (grams) | | | 16.7 |
| Water (grams) | 83.3 | 83.3 | 83.3 |
| Property | | | |
| Viscosity (cPs) | 69000 | 75500 | 65000 |

Example 9

Use of Network Polymer Composition II as an Aqueous Phase Thickener

The thickened aqueous compositions of Example 9 were made by combining the listed ingredients in the relative amounts set forth in Table IX, according to the following procedures. Network Polymer Composition II prepared according to Example 2 was missed with D.I. water using an overhead mixer at 700 RPM for 10 minutes. The viscosities of the resulting materials (measured after 24 hours) are listed in Table IX.

TABLE IX

| | Sample 10 |
|---|---|
| Ingredients | |
| Network polymer composition II (grams) | 20 |
| Water (grams) | 80 |
| Property | |
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 10

Use of Network Polymer Composition II as an Aqueous Phase Thickener

The thickened aqueous compositions of Example 10 were made by combining the listed ingredients in the relative amounts set forth in Table X, according to the following procedures. Network Polymer Composition I prepared according to Example 2 was missed with D.I. water using an overhead mixer at 700 RPM for 10 minutes. pH was adjusted by using glycolic acid. The viscosities of the resulting materials (measured after 24 hours) are listed in Table X. Network Polymer Composition II provided effective thickening of the aqueous solution in the range of pH 4-9.

TABLE X

| Ingredients | Sample 10 |
|---|---|
| Network polymer composition II (grams) | 20 |
| Water (grams) | 80 |
| Property | |
| Viscosity at pH 4 (cPs) | 67500 |
| Viscosity at pH 5 (cPs) | 69000 |
| Viscosity at pH 6 (cPs) | 70500 |
| Viscosity at pH 7 (cPs) | 79000 |
| Viscosity at pH 9 (cPs) | 84000 |

Example 11

Use of Network Polymer Compositions I-V in Moisturizer Compositions

The moisturizing formulations of Example 11 were made by combining the listed ingredients in the relative amounts set forth in Table XI, according to the following procedures. Network Polymer Composition I-V were prepared according to Example 1-5 respectively. The ingredients were mixed using an overhead mixer at 700 RPM for 10 minutes. Panel tests showed that Sample 11-2 to 11-5, when applied on skin, provided significantly lower tack, lighter and more cushioning feel than Comparative Sample 11.

TABLE XI

| Ingredients | Sample 11-1 | Sample 11-2 | Sample 11-3 | Sample 11-4 | Sample 11-5 | Comparative Sample 11 |
|---|---|---|---|---|---|---|
| Network polymer composition I (grams) | 15 | | | | | |
| Network polymer composition II (grams) | | 15 | | | | |
| Network polymer composition III (grams) | | | 15 | | | |
| Network polymer composition IV (grams) | | | | 15 | | |
| Network polymer composition V (grams) | | | | | 15 | |
| Hispagel 200 | | | | | | 15 |
| Glycerin | 20 | 20 | 20 | 20 | 20 | 20 |
| Water (grams) | 65 | 65 | 65 | 65 | 65 | 65 |

Example 12

Use of Network Polymer Compositions I in a Sunscreen Lotion Composition

The sunscreen lotion compositions in Example 12 were made by combining the ingredients listed in Table XII, according to the following procedure: (1) Part A was made by mixing all the ingredients using an overhead mixer at 700 RPM until uniform; (2) Part B was mixed in a separate container and then added to Part A; (3) the mixture was then mixed until uniform. Stable o/w emulsions were prepared. Sample 12 provided a lighter and silkier feel than Comparative Sample 12. It also exhibited lower tack.

TABLE XII

| Ingredients | Sample 12 Weight (grams) | Comparative Sample 12 Weight (grams) |
|---|---|---|
| Part A | | |
| Network polymer composition I | 8 | |
| *Pemulen TR-2 | | 0.2 |
| Water | 26 | 33.8 |
| Glycerin | 2 | 2 |
| Part B | | |
| Octyl methoxycinnamate | 3 | 3 |
| Octyl salicylate | 1 | 1 |

*Pemulen TR-2 is an Acrylates/C10-30 Alkyl Acrylate Crosspolymer, available Lubrizol.

Example 13

Use of Network Polymer Compositions I in a Color Cosmetic Composition

The color cosmetic compositions in Example 13 were made by combining the ingredients listed in Table XIII and mixing using an overhead mixer until uniform. Panel test showed that Sample 13, when applied on skin, exhibited better spreading and sensory than Comparative Example 13.

TABLE XIII

| Ingredients Part A | Sample 13 Weight (grams) | Comparative Sample 13 Weight (grams) |
|---|---|---|
| Network polymer composition I | 20 | |
| *Hispagel | | 20 |
| Water | 77 | 77 |
| **Aeroxide TiO₂ P25 | 3 | 3 |

*Hispagel 200 is a glycerin polyacrylate, available at Cognis.
**Aeroxide TiO₂ P25 is a titanium dioxide, available of Evonik Degussa.

Example 14

Use of Network Polymer Compositions I in a Rinse-off Hair Conditioner Composition The rinse-off hair conditioner compositions of Sample 14 and Comparative Example 14 were made by combining the ingredients listed in Table XIV, according to the following procedure: (1) Part A was made by combining the ingredients and mixing at 60° C. until uniform; (2) Part B was mixed in a separate container and then added to Part A; (3) the mixture was then mixed until uniform. Panel tests showed that Network Polymer Composition I improved the softness and sleekness of the hair.

TABLE XIV

| Ingredients | Sample 14 Weight (grams) | Comparative Sample 14 Weight (grams) |
|---|---|---|
| Part A | | |
| Network polymer composition I | 25.5 | 0 |
| *SF1632 | 5 | 5 |
| D.I. water | 59.5 | 85 |
| **Tergitol TMN-6* | 0.1 | 0.1 |
| Part B | | |
| D.I. water | 9.8 | 9.8 |
| ***Polyquaternium-10 (Ucare polymer JR30M) | 1 | 1 |

*SF1632-C16-18 alkyl dimethicone, available at GE silicones;
**Tergital TMN-6 is a Branched Secondary Alcohol Ethoxylates, available at Dow Chemicals;
***Polyquaternium-10 UCARE polymer JR30M, available at Dow Chemicals.

Example 15

Preparation of Network Polymer Composition XV

Mixture 1 through 4 in Table XV were used to prepare Network Polymer Composition I. Mixture 1 was placed in a 2 L mixer. Nitrogen was bubbled through for 30 minutes to remove oxygen from the system. The mixture was heated to 55° C. under nitrogen and held at the temperature. Mixture 2 and mixture 3 were added over a 5- minute time period. The mixture was cooled to 25° C. after two hours. Mixture 4 was then added and the mixture was mixed for 30 minutes to give an off-white soft solid. The soft solids were then mixed with acetone in 1:4 weight ratios for 30 minutes. The mixture was allowed to settle for 30 minutes. The liquid layer was then decanted. The solids were dried in a vacuum oven at 80° C. for two hours and then grinded with a coffee grinder to obtain a white powder.

TABLE XV

| INGREDIENTS | WEIGHT (grams) |
|---|---|
| Mixture 1 | |
| Acrylic acid | 2.8 |
| Phosphoric acid mono-ester of polypropylene glycol mono-methacrylate (MW = 500) | 108.0 |
| Phosphoric acid di-ester of polypropylene glycol mono-methacrylate (MW = 900) | 11.0 |
| Polyproplyeneglycol mono-methacrylate (MW = 400) | 5.0 |
| *Tergital TMN-6 | 5.0 |
| Water | 338.7 |
| Sodium hydroxide solution (40 wt % in water) | 28.4 |
| Mixture 2 | |
| Sodium bisulfite solution (10% in water) | 1.3 |
| Ferrous ammonium sulfate solution (0.2% in water) | 2.5 |
| Mixture 3 | |
| Potassium persulfate solution (4.5 wt % in water) | 15.0 |
| Mixture 4 | |
| Sodium metabisulfite solution (10 wt % in water) | 25.0 |

*Tergital TMN-6 is a Branched Secondary Alcohol Ethoxylates, available at Dow Chemicals

Example 16

Use of Network Polymer Compositions XV in a Moisturizer Composition

The moisturizing formulations of Example 16 were made by combining the listed ingredients in the relative amounts set forth in Table XVI, according to the following procedures. Network Polymer Composition XV were prepared according to Example 15. The ingredients were mixed using Speed mixer at 3000 RPM for 2 minutes. Panel tests showed that Sample 16, when applied on skin, provided lower after-rub-in tack and more cushioning feel than Comparative Sample 16-1. Comparative sample 16-2 was not a stable mixture.

TABLE XVI

| Ingredients | Sample 16 Weight (grams) | Comparative Sample 16A Weight (grams) | Comparative Sample 16B Weight (grams) |
|---|---|---|---|
| Network polymer composition XV | 0.5 | 0.5 | 0 |
| Glycerin | 1 | 1 | 1 |
| D.I. water | 7 | 8.5 | 7.5 |
| *Velvesil 125 | 1.5 | 0 | 1 |

*Velvesil 125 is a silicone gel product, available at Momentive Performance Materials.

Results:
Result Summary:
Examples 1-5, 15 presented six synthesis examples, each representing a different structure. Examples 6-10 showed how these polymer network compositions thickened water at different solids levels or pH. Example 11 proved that the polymer network composition of the present invention could significantly improve the sensory of a moisturizer formulation, compared with Hispagel 2000, a benchmark product. In Example 12, the polymer network composition showed to provide a lighter, silkier sensory in a sunscreen formulation, as well as oil-in-water emulsifying capability. Example 13 showed that the polymer could help to disperse hydrophilic pigment in a color cosmetic formulation. Example 14 showed that this polymer network composition could bring the softness and sleekness feels to hair when incorporated in a rinse-off hair conditioner formulation. Example 15 showed a synergistic effect between the present structure and a silicone gel.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

What is claimed is:

1. A personal care product composition comprising a crosslinked network polymer provided by the reaction of
   (i) at least one anionic polymerizable ethylenically unsaturated monomer (I) selected from the group consisting of $$[CH_2=C(R_3)C(O)OX_a(C_2H_4O)_b(C_3H_6O)_c(C_4H_8O)_d]_pP(O)(OY)_q(OZ)_r$$

where
   $R_3$=H or alkyl of 1 to about 6 carbon atoms;
   X=alkyl, aryl, or alkaryl diradical connecting group of 0 to about 9 carbon atoms; a is 0 to about 100;
   b is 0 to about 100;
   c is 0 to about 100;
   d is 0 to about 100;
   q is 0 to about 2;
   r is 0 to about 2;
   p is 1 to about 3 subject to the limitation that p+q+r=3; and
   Y and Z is H, or metal ion;
   wherein at least one of b, c, and d is from 8 to 50; and

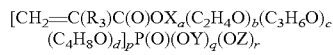

where
   $R_3$=H or alkyl of from 1 to about 6 carbon atoms;
   X=alkyl, aryl, or alkaryl diradical connecting group of 0 to about 9 carbon atoms;
   a' is 0 to about 100;
   b' is 0 to about 100;
   c' is 0 to about 100;
   d' is 0 to about 100;
   Y is H, or metal ion;
   wherein at least one of b', c', and d' is from 8 to 50; and
   (ii) one or more additional monomers (II) selected from the group consisting of acrylic acid/acrylate, methacrylic acid/methacrylate, acrylamides, vinyl acetate and styrene, which are copolymerizable with (I); and
   (iii) a cross-linking agent (III), containing at least one ethylenically unsaturated group and capable of copolymerizing with (I) and (II), wherein the network polymer is simultaneously polymerized and cross-linked; and
   wherein the personal care product composition has an oil and/or water swellability of 5 to 500 times its original volume,
   the personal care product composition is swollen by water to form a solid or gel, and
   the personal care product composition has improved sensory feeling through use of water.

2. The personal care product composition of claim 1 wherein said cross-linking agent is a polyfunctional vinylidene monomer containing at least two unsaturated groups.

3. The personal care product composition of claim 2 said polyfunctional vinylidene monomer is selected from the group consisting of butadiene, isoprene, divinyl benzene, allyl acrylates, polyalkylene glycol diacrylates and dimethacrylates, diallyl esters, and dimethallyl esters.

4. The personal care product composition of claim 1 wherein said composition comprises about 40 to about 99 weight percent based on the total weight of the monomers of said at least one anionic polymerizable ethylenically unsaturated monomer (I), about 0.5 to about 50 weight percent based on the total weight of the monomers of said additional monomers and about 0.1 to about 10 weight percent based on the total weight of the monomers of said cross-linking agent.

5. The personal care product composition of claim 1 wherein d, and d' are from 1 to 50.

6. The personal care product composition of claim 1 wherein said cross-linking agent (III) is at least one anionic polymerizable ethylenically unsaturated monomer (I) selected from the group consisting of

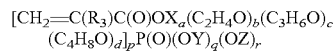

where
$R_3$=H or alkyl of 1 to about 6 carbon atoms;
X=alkyl, aryl, or alkaryl diradical connecting group of 0 to about 9 carbon atoms;
a is 0 to about 100;
b is 0 to about 100;
c is 0 to about 100;
d is 0 to about 100;
q is 0 or 1;
r is 0 or 1; and
p is 2 to about 3 subject to the limitation that p+q+r=3;
Y and Z is H, or metal ion.

7. The personal care product composition of claim 1 wherein said at least one anionic polymerizable ethylenically unsaturated monomer (I) is selected from the group consisting of $CH_2=C(CH_3)C(O)O(C_3H_6O)_6P(O)(OH)(ONa)$, $CH_2=C(CH_3)C(O)O(C_3H_6O)_6P(O)(OH)_2$, $CH_2=CHC(O)O(C_3H_6O)_6P(O)(OH)(OH)_2$, and $CH_2=C(CH_3)C(O)O(C_2H_4O)_nP(O)(OH)_2$;
said one or more additional monomers (II) are selected from the group consisting of: $CH_2=CHC(O)OH$ and $CH_2=C(CH_3)C(O)O(C_3H_6O)_6H$; and
said cross-linking agent (III) is selected from the group consisting of $CH_2=CHC(O)O(C_2H_4O)_nC(O)OCH=CH_2$, $[CH_2=C(CH_3)CO_2CH_2]_3CC_2H_5$ and $[CH_2=C(CH_3)C(O)O(C_3H_6O)_6]_2P(O)(OH)$ and
wherein said composition further comprises water.

8. A personal care product comprising the composition of claim 1 wherein the personal care formulation is selected from the group consisting of deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail-and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprising at least one of the foregoing applications.

9. The personal care product composition of claim 8 further comprising personal care ingredient selected from the group consisting of emollient, moisturizer, humectant, pigment, coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, and combinations thereof.

10. The personal care product composition of claim 9 further comprising at least one additive selected from the group consisting of surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, film formers, thickening agents, particulate fillers, silicones, clays, plasticizers, humectants, occlusives, sensory enhancers, esters, resins, film formers, film forming emulsifiers and high refractive index materials.

11. The product composition of claim 1 wherein at least one of b, c, and d is from 1 to about 50.

12. The product composition of claim 11 wherein d is at least 1.

13. The product composition of claim 1 wherein at least one of Y and Z is a metal ion.

14. The product composition of claim 11 wherein at least one of Y and Z is a metal ion.

15. The personal care product composition of claim 1, when applied to skin, provides significantly low tack of the skin.

16. The personal care product composition of claim 1, when applied to hair, improves sleekness of the hair.

\* \* \* \* \*